US012714239B1

(12) United States Patent
Sweeney

(10) Patent No.: US 12,714,239 B1
(45) Date of Patent: Aug. 25, 2026

(54) INNOVATIVE CRIB

(71) Applicant: Chace Sweeney, Vestavia Hills, AL (US)

(72) Inventor: Chace Sweeney, Vestavia Hills, AL (US)

( * ) Notice: Subject to any disclaimer, the term of this patent is extended or adjusted under 35 U.S.C. 154(b) by 0 days.

(21) Appl. No.: 18/921,854

(22) Filed: Oct. 21, 2024

Related U.S. Application Data

(60) Provisional application No. 63/544,824, filed on Oct. 19, 2023.

(51) Int. Cl.
*A47D 7/02* (2006.01)
*A61M 21/02* (2006.01)
*E05F 15/70* (2015.01)

(52) U.S. Cl.
CPC ............... *A47D 7/02* (2013.01); *A61M 21/02* (2013.01); *E05F 15/70* (2015.01)

(58) Field of Classification Search
CPC ....................................................... E05F 15/70
USPC ............................................................. 5/100
See application file for complete search history.

(56) References Cited

U.S. PATENT DOCUMENTS 2,059,240 A * 11/1936 Johnston .................. A47D 7/00 182/20
5,926,870 A * 7/1999 Branca-Barnes ........ A47D 7/02 5/100
6,433,699 B1 * 8/2002 Slomowitz ............. G08B 21/24 340/539.1
8,646,126 B2 * 2/2014 Carta ....................... A47D 7/02 5/100
10,188,222 B2 * 1/2019 Veron ................ G08B 21/0205
2003/0038725 A1 * 2/2003 Slomowitz ............... A47D 7/02 340/686.1
2022/0378222 A1 * 12/2022 Cerilli ...................... A47D 7/01

* cited by examiner

*Primary Examiner* — David R Hare
*Assistant Examiner* — Joseane E. Tejada
(74) *Attorney, Agent, or Firm* — Kenneth L. Tolar

(57) ABSTRACT

A crib includes a support frame having a bottom surface and a plurality of upstanding sidewalls that form an enclosed sleeping chamber. The sleeping chamber is dimensioned to accommodate both an adult and a child. One of the sidewalls includes a gate that obstructs an access opening for an adult to enter and exit the sleeping chamber. Gate operation can be performed manually or automatically with a control module. The control module also includes a means for playing soothing sound recordings to lull a child to sleep. Accordingly, an adult can enter the crib and lie next to a child until he or she falls asleep. The adult can easily exit the sleeping chamber and quietly close the access gate without moving or disturbing the child.

11 Claims, 3 Drawing Sheets

30
1
7

1
3
6

1
3
6
20
6
1
3
2

1
5
25
6

6
1
2

INNOVATIVE CRIB

CROSS REFERENCE TO RELATED APPLICATIONS

This application claims priority of provisional application No. 63/544,824 filed on Oct. 19, 2024, the specification of which is incorporated herein by reference.

BACKGROUND OF THE INVENTION

Disclosed herein is a uniquely designed crib that can comfortably accommodate an adult or caregiver until the child falls asleep.

DESCRIPTION OF THE PRIOR ART

Small children often resist falling asleep unless comforted by an adult while lying on a couch, a chair, or an adult bed. Once the child falls asleep, the adult must transfer the child to a crib to sleep in a secure environment. However, during the transfer, the child is often startled and awakened, requiring the adult to repeat the process, which is burdensome and annoying. Furthermore, if the adult instead falls asleep before the transfer, the child can easily fall or crawl away, causing serious injury. Ideally, a child should be lulled to sleep in a final bedding location, i.e., the child's crib. However, a conventional crib is too small and fragile to allow a parent or caregiver to lie next to a child.

Accordingly, there is currently a need for a crib that can accommodate both a child and a caregiver to safely and effectively lull a child to sleep in a secure environment. The disclosed device addresses this need by providing a larger, sturdier crib having a hinged or stowable access gate that allows the parent to quietly exit the crib once the child has fallen asleep.

SUMMARY OF THE INVENTION

The present disclosure relates to a crib comprising a support frame having a bottom surface and a plurality of upstanding sidewalls that form an enclosed sleeping chamber. The sleeping chamber is dimensioned to accommodate both an adult and a baby. One of the sidewalls includes a gate that obstructs an access opening for an adult to enter and exit the sleeping chamber. Gate operation can be performed manually or automatically with a control module. The control module also includes a means for playing soothing sound recordings to entice a child to fall asleep. Accordingly, an adult can enter the crib and lie next to the child until he or she falls asleep. The adult can easily exit the sleeping chamber and quietly close the access gate without relocating or disturbing the child.

It is therefore an object of the present invention to provide a crib that can comfortably accommodate an adult until the child falls asleep.

It is therefore another object of the present invention to provide a crib that can be quickly and easily converted to a child or toddler's bed.

It is therefore yet another object of the present invention to provide a crib having an access gate that can be automatically opened.

Other objects, features, and advantages of the present invention will become readily apparent from the following detailed description of the preferred embodiment when considered with the attached drawings and the appended claims.

BRIEF DESCRIPTION OF THE DRA WINGS

DESCRIPTION OF THE PREFERRED EMBODIMENT

Figures 1, 2:
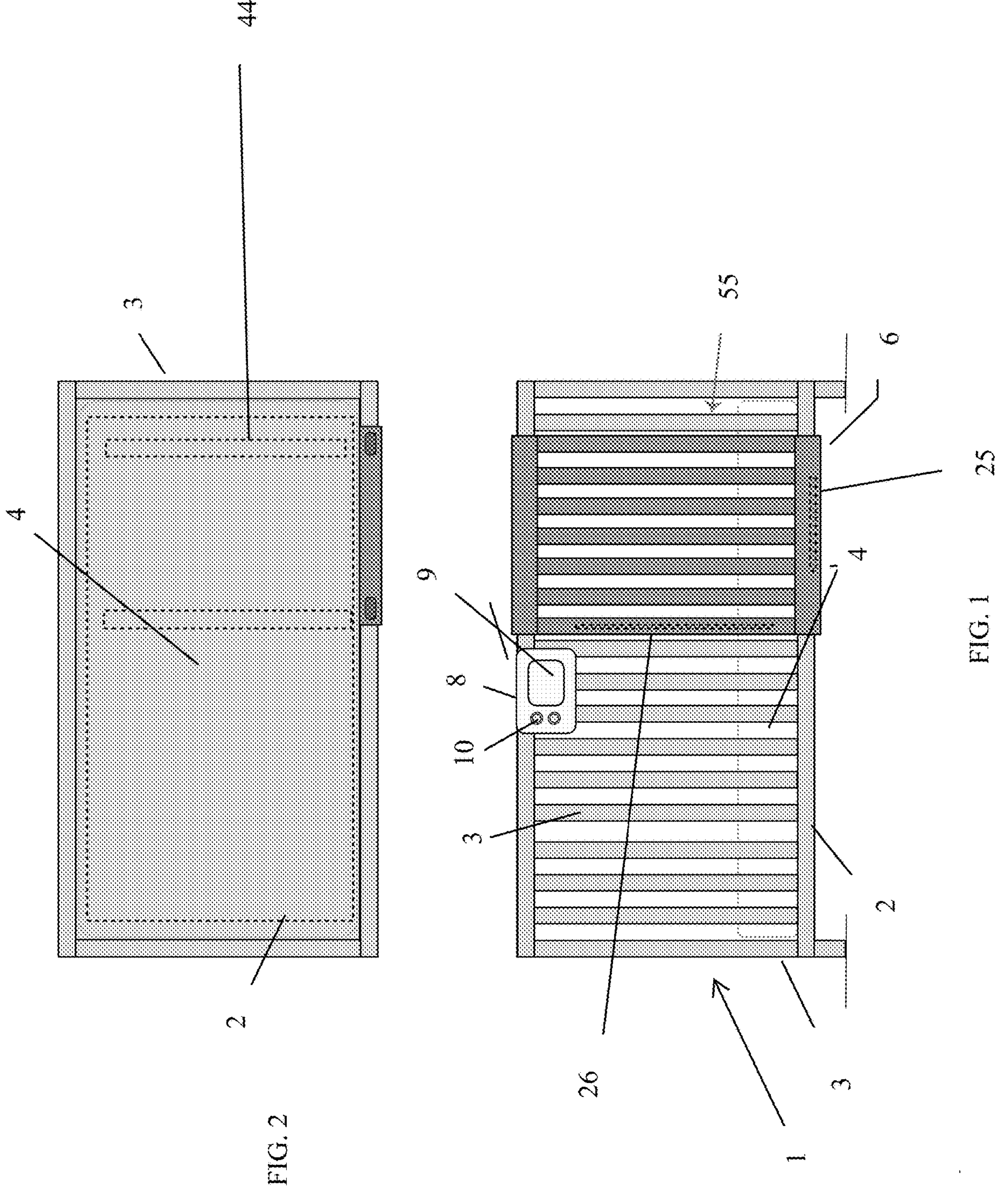
FIG. 1 is a front, plan view of the crib according to the present invention.
FIG. 2 is a top, plan view of the crib.

Disclosed herein is a crib comprising a support frame 1 having a bottom surface 2 and a plurality of upstanding sidewalls 3 that form an enclosed sleeping chamber. The sidewalls may be formed of spaced rails 55 to allow a user to see into and out of the crib. A mattress 4 positioned on the bottom surface 2 is dimensioned to accommodate both an adult and a child. For example, the mattress could be a standard or XL twin mattress allowing it to be used elsewhere if desired. The bottom surface 2 is vertically adjustable to allow the mattress height to be varied as desired. The support frame is constructed with hardwood or a similar equivalent that can withstand a load of at least 450 pounds so that both a child and an adult can safely lie on the mattress without fear of damage or collapse.

Figures 3, 4, 5, 6, 7, 8:
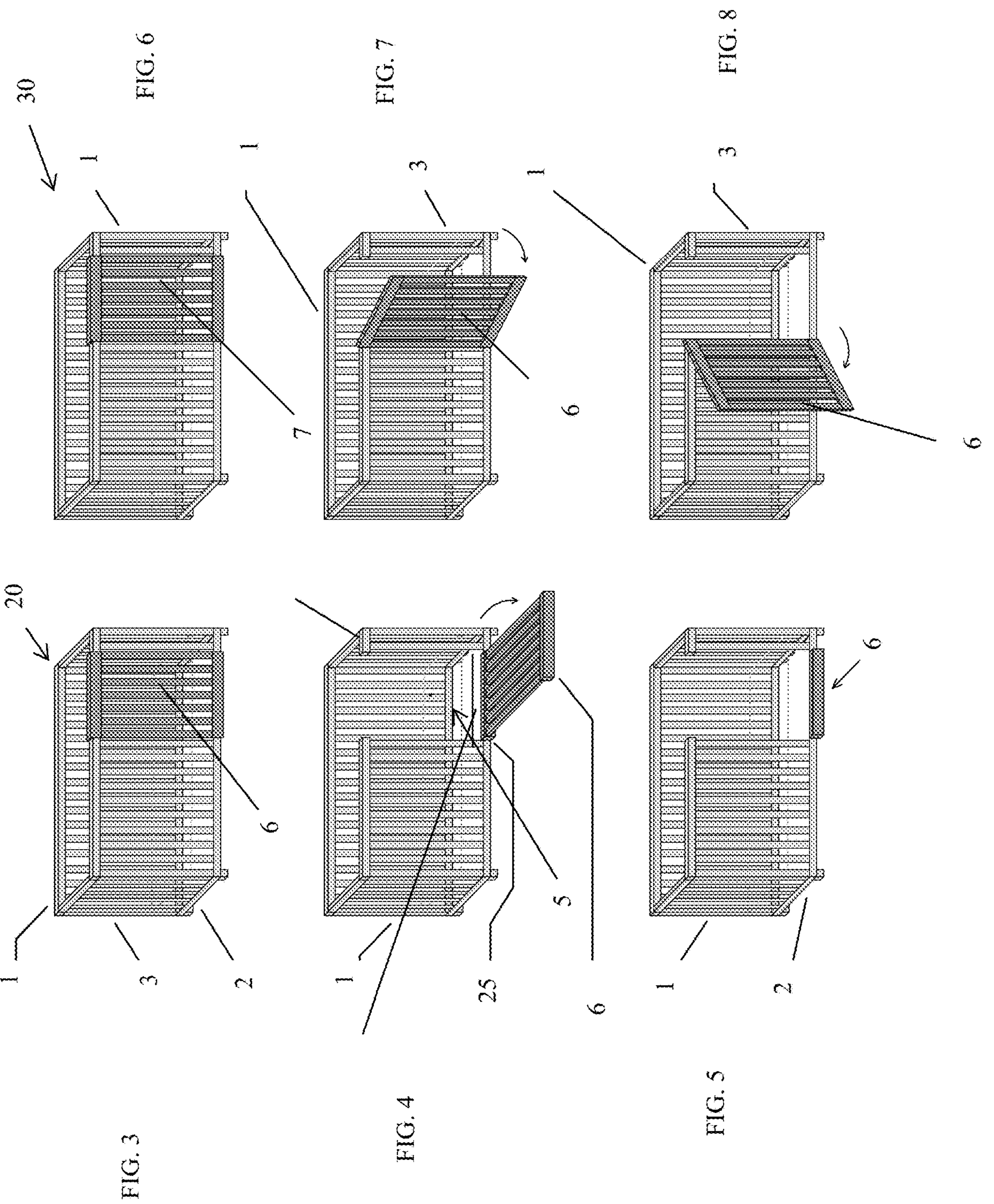
FIGS. 3-5 depict the steps of releasing and stowing the access gate according to a first embodiment of the present invention.
FIGS. 6-8 depict the steps of opening the gate according to a second embodiment of the present invention.
Figure 9:
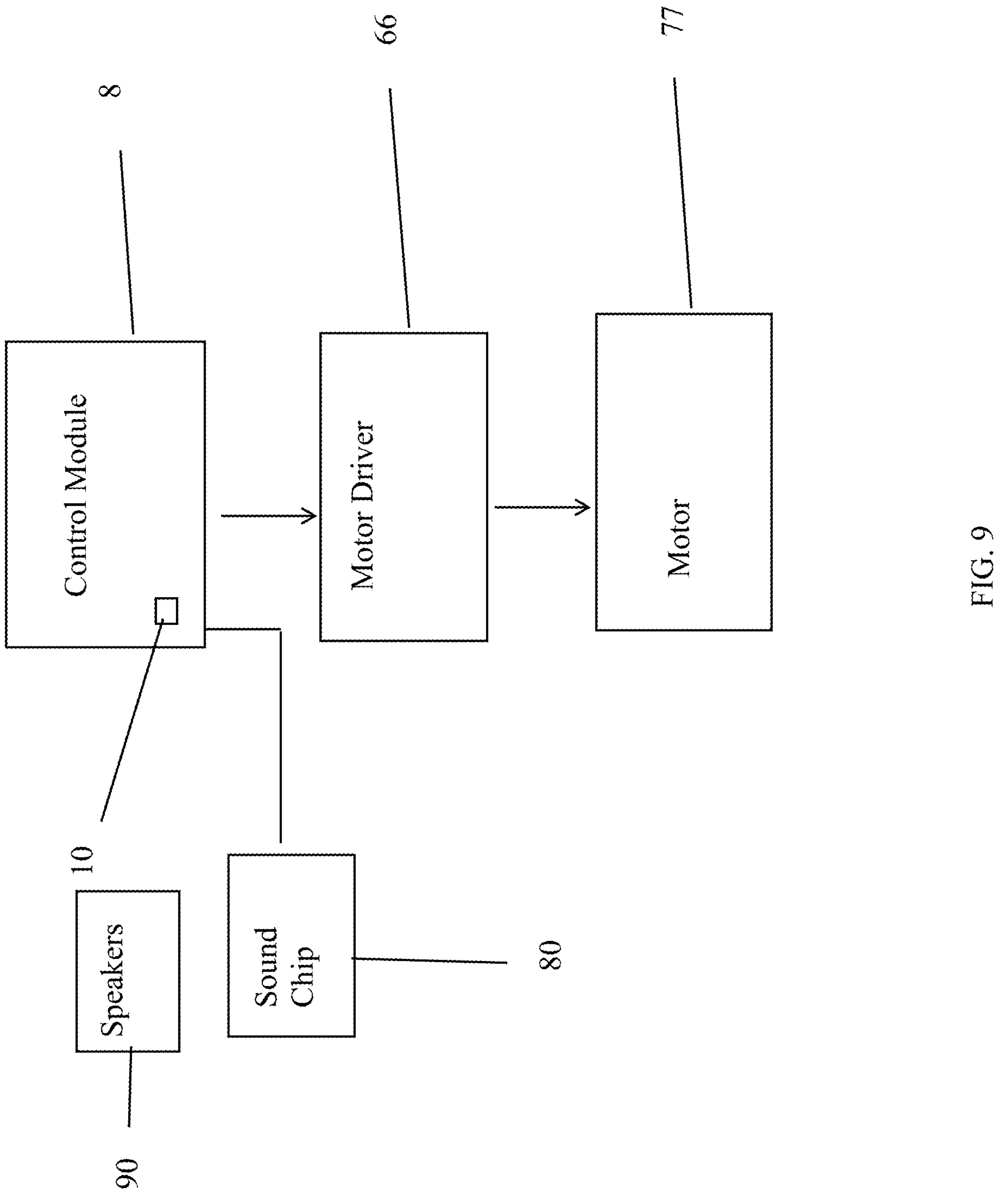
FIG. 9 depicts a flow chart of the automated control module.

Now referring to FIGS. 3-5, a portion of one of the sidewalls includes a an access opening 5 for an adult to enter and exit the sleeping chamber. A first embodiment 20 includes the gate 6 positioned within the access opening having hinges 25 on a bottom edge that allow it to be pivoted downwardly to a horizontal position. Tracks 44 allow the gate 6 to be stowed beneath the frame once in the horizontal position. In the stowed position, the crib can be used as a bed for a toddler or an older child to maximize versatility.

Now referring to FIGS. 6-8, in a second embodiment 30, the gate 7 includes hinges 26 on either or both of two side edges in lieu of or in addition to the hinges on lower edge, allowing it to pivot in a horizontal plane between opened and closed positions to provide access to the sleeping chamber. The gate hinges 26 include a spring mechanism that closes the gate 7 when positioned at or less than a predetermined angle relative to the sidewall. When the gate 7 is oriented above the predetermined angle, a detent mechanism maintains the gate 7 in the open position to facilitate easy access and egress. The hinges 25. 26 are friction dampened to assure smooth, quiet movement and to prevent the gate from slamming so as not to disturb a sleeping child. The gate 7 can also be completely removed to convert the crib to a child or toddler bed, if desired.

Gate 6, 7 operation can be performed manually, or automatically with a control module 8 attached to an upper beam on one of the sidewalls. The control module 8 includes a display 9 on a front surface with control buttons 10 adjacent thereto. The control module 8 further includes a motor driver 66 and a microprocessor that communicate with a motor 77 upon depressing one of the control buttons 10 to automatically pivot or lower the access gate as desired. The control module 8 also includes speakers 90 and an internal sound chip 80 for playing soothing music, white noise, or similar background recordings to entice a child to fall asleep. The display depicts a touch-screen menu for controlling the sound chip output, speaker volume, etc.

Accordingly, an adult can enter the crib and console the child until he or she falls asleep. The adult can easily exit the sleeping chamber and quietly close the access gate without moving or disturbing the child.

The above-described device is not limited to the exact details of construction and enumeration of parts provided herein. Furthermore, the size, shape, and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A crib comprising:

a support frame having a bottom surface and a plurality of upstanding sidewalls that form an enclosed sleeping chamber;

an access opening on a portion of one of said sidewalls;

a mattress positioned on the bottom surface, said mattress dimensioned to accommodate both an adult and a child;

a gate obstructing an access opening, said gate pivotable onto and away from said access opening to provide selective access to said sleeping chamber; and further comprising a control module attached to one of said sidewalls, wherein said control module includes at least one control button that operates a motor for automatically pivoting said gate.

2. The crib according to claim 1 wherein said gate is laterally pivotal.

3. The crib according to claim 1 wherein said gate is pivotal downwardly to a horizontal position.

4. The crib according to claim 3 further comprising tracks beneath said bottom surface for slidably receiving said gate when in the horizontal position to allow said gate to be stowed beneath said frame.

5. The crib according to claim 1 wherein said mattress is a twin-bed sized mattress, allowing said crib to be used by a toddler, or said mattress to be removed and used in another location if desired.

6. The crib according to claim 1, wherein said support frame is constructed to withstand a load of at least 450 pounds so that both a child and an adult can safely lie on the mattress without risk of damage or collapse.

7. The crib according to claim 1 wherein said gate includes hinges on a bottom edge that allow said gate to be pivoted downwardly to a horizontal position.

8. The crib according to claim 2 wherein said gate includes hinges on either or both of two side edges, allowing said gate to pivot in a horizontal plane between opened and closed positions to provide access to the sleeping chamber.

9. The crib according to claim 8 wherein said hinges include a spring mechanism that closes said gate when positioned at a predetermined angle relative to the sidewall.

10. The crib according to claim 9 wherein said hinges are friction dampened to assure smooth, quiet movement and to prevent the gate from slamming so as not to disturb a sleeping child.

11. The crib according to claim 1 wherein said control module includes speakers and a sound chip for playing background recordings to entice a child to fall asleep.

* * * * *